United States Patent [19]

Phillips

[11] Patent Number: 5,181,933
[45] Date of Patent: Jan. 26, 1993

[54] SPLIT FOOT PROSTHESIS

[76] Inventor: Van L. Phillips, 5499 Avenida Maravillas, Rancho Santa Fe, Calif. 92067

[21] Appl. No.: 662,928

[22] Filed: Feb. 28, 1991

[51] Int. Cl.[5] .............................................. A61F 2/66
[52] U.S. Cl. ...................................... 623/55; 623/52
[58] Field of Search ................................ 623/53-56, 623/27, 47-56

[56] References Cited

U.S. PATENT DOCUMENTS

| 65,187 | 5/1867 | Emery | 623/52 |
|---|---|---|---|
| 951,989 | 3/1910 | Hanger | 623/56 |
| 2,036,830 | 4/1936 | Rowley | 623/54 |
| 2,197,093 | 4/1940 | Campbell | 623/56 |
| 2,475,372 | 7/1949 | Catranis | 623/54 X |
| 4,547,913 | 10/1985 | Phillips | 623/53 X |
| 4,645,509 | 2/1987 | Poggi et al. | 623/55 |
| 4,676,801 | 6/1987 | Lundeen | 623/53 |
| 4,822,363 | 4/1989 | Phillips | 623/27 |
| 4,938,776 | 7/1990 | Masinter | 623/49 |

FOREIGN PATENT DOCUMENTS

| 0325171 | 9/1920 | Fed. Rep. of Germany | 623/53 |
|---|---|---|---|
| 0963849 | 5/1957 | Fed. Rep. of Germany | 623/27 |
| 1498490 | 8/1989 | U.S.S.R. | 623/53 |
| 0306313 | 2/1929 | United Kingdom | 623/53 |
| 8905617 | 6/1989 | World Int. Prop. O. | 623/53 |

Primary Examiner—Randy C. Shay
Assistant Examiner—D. Willse
Attorney, Agent, or Firm—J. Mark Holland; Thomas P. Mahoney

[57] ABSTRACT

A prosthetic foot is characterized by an attachment section and plurality of curvilinear foot portions extending downwardly from the attachment section to contact a supporting surface. The portions are capable of movement independent from one another. Preferably, the plurality of foot portions is fabricated by dividing a forefoot portion and a heel portion demountably attached thereto. Such division may be achieved by the provision of a slot in said forefoot and heel portions. A strap or similar expedient is provided to limit the movement of the foot portions relative to each other.

20 Claims, 2 Drawing Sheets

SPLIT FOOT PROSTHESIS

BACKGROUND OF THE INVENTION

This invention relates to foot prostheses in general, and specifically to a split prosthetic foot which incorporates a plurality of curvilinear foot portions which co-operate with one another to provide the wearer with performance characteristics not available from prior art prostheses.

A number of prosthetic devices have attempted to provide energy-storing and -releasing functions to simulate ambulation on a natural limb. For example, see my U.S. Pat. No. 4,547,913 for my invention relating to a "Composite Prosthetic Foot and Leg", and U.S. Pat. No. 4,822,363 for my invention relating to a "Modular Composite Prosthetic Foot and Leg". Also, my pending applications Ser. Nos. 07/337,374, 07/585,920 and 07/293,824, now U.S. Pat. No. 5,037,444, disclose prosthetic foot devices with similar preferred materials and methods of manufacture, and with corresponding benefits therefrom.

Each of my aforementioned inventions is characterized by lightweight, elongated structures incorporating polymer impregnation of superimposed reinforcing laminae maintained in the desired configuration. Such configurations and constructions provide the desirable characteristics of strength and flexibility in the prosthetic member, and achieve a simulation of the performance of natural feet which had previously not been attainable. Such prostheses may be provided in modular assemblies, whereby the particular performance characteristics of a given prosthesis may be adapted and readily adjusted to meet the needs and activity level of the individual patient.

Other prosthetic foot devices include U.S. Pat. No. 3,335,428 to Gajdos, which attempts to duplicate the skeletal and skin structure of a natural human foot, U.S. Pat. No. 2,075,583 to Lange, which incorporates a rubber form mounted in operative relationship with a rigid metallic core, and U.S. Pat. No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

Although several of the aforementioned prostheses have provided flexure in a fore-and-aft direction, such prior art devices are relatively stiff and unresponsive with respect to torsional loading which might result from leaning to one side or from ambulation in a direction other than straight ahead. In fact, such prostheses provide a consistent energy response for loading at any given fore-and-aft location on the prosthesis, regardless of whether the loading occurs at one edge of the prosthesis or at the center thereof.

OBJECTS AND ADVANTAGES OF THE INVENTION

It is, therefore, an object of my invention to provide a prosthetic foot which provides a varying energy-absorbing and energy-storing performance dependent upon the lateral location of the contact between the foot and an underlying supporting surface, as well as the angle of impact therebetween. In particular, the prosthesis of my invention incorporates a plurality of foot portions capable of movement independently from one another.

In a preferred embodiment, as described below, the foot portions are fabricated by providing a slot through virtually the entire prosthesis, effectively dividing it into two independent prostheses. When both of these independent portions are similarly loaded and stressed, such as during straight-ahead walking, the portions cooperate and act in unison to achieve a performance similar to a foot with no division therein. When the prosthesis of my invention undergoes lateral loading, however, the various portions may act independently from one another and thereby provide performance characteristics which may vary substantially from those of a foot with no division therein.

In effect, the prosthesis of my invention simulates the sideways turning of a natural ankle, in that it permits the energy-storing structure of the entire foot to twist slightly from side to side in response to various loading conditions.

Moreover, such independent movement provides additional effective contact area between the bottom of the prosthesis and a confronting supporting surface, under the aforementioned lateral loading conditions. Instead of a single outer edge of the prosthesis contacting the supporting surface, two or more "edges" may achieve such contact, improving the traction or frictional interaction of the prosthesis on the surface.

Another object of my invention is the provision of a prosthetic foot of the aforementioned character which includes connecting or retaining means such as a strap for limiting the movement of the relevant independent foot portions, or selected ones of them, with respect to one another. This insures that the energy-storing capabilities of the entire foot are utilized when the foot is placed under conditions of extreme lateral stresses. In such situations, the connecting means effectively connects selected of the foot portions with a predetermined amount of play therebetween, whereby after one of the connected portions has been displaced that predetermined distance with respect to the other, the strap will require that both connected portions be simultaneously actuated in order for further displacement in that direction to occur.

It is a further object of my invention to provide a prosthetic foot of the aforementioned character which is of modular configuration, resulting in ready assembly and adjustability thereof. The foot of my invention preferably includes forefoot and heel portions that can be readily exchanged with correspondingly-constructed forefoot and heel portions to provide size adjustment or different spring rates to suit the size of foot of the amputee or the stride, height, weight, and activity level of the amputee. Therefore, a range of combinations of spring rate and size can be provided to the amputee, achieving a natural stride and resilience of gait.

Another object of the invention is the provision of a prosthetic foot of the aforementioned character in which the forefoot and heel portions of the prosthesis are fabricated from superimposed laminates maintained in operative relationship by an encapsulating polymer, and further in which said foot is susceptible to bending stress determined by the number of the laminates and polymers in the respective element. Thus, the laminates are encapsulated in a polymer and capable of spring stress response as loads are imposed thereupon during the utilization of said foot.

A further object of the invention is the provision of a prosthetic foot of the aforementioned character which consists of continuous, integrally and simultaneously formed attachment, ankle, arch and toe sections of a forefoot portion, and attachment and heel sections of a heel portion, said sections being respectively fabricated as unitary structures by polymer impregnation of superimposed reinforcing laminae maintained in the desired configuration of said foot and said sections being capable of spring stress generated energy storage whereby the subjection of the prosthetic foot to bending moments will cause uniform transmission of spring stress through said sections of said foot.

The polymers utilized to encapsulate the fibrous laminae are characterized by elasticity and flexibility so that the foot prosthesis deflects proportionally to the engagement of said prosthetic foot with an adjacent surface, causing the resultant energy to be stored and subsequently released when the gait of the amputee incorporating thrust and lift components results in the utilization of the stored energy and a consequent reduction of the energy expended by the amputee.

In order to impart a cosmetic aspect to the prosthetic foot, after proper fitting of the foot to insure that it is properly balanced and of appropriate size, the prosthesis may be encapsulated in a suitably shaped cosmetic shroud. The shroud must be sufficiently flexible so as not to inhibit the free movement and flexure of the foot, but, because of the inherently resilient and stress-absorbing characteristics of said foot little dependence is needed upon the ancillary cushioning action of the shroud.

Other objects and advantages of the invention will be apparent from the following specification and the accompanying drawings, which are for the purpose of illustration only.

DESCRIPTION OF PREFERRED EMBODIMENT

Figure 1:
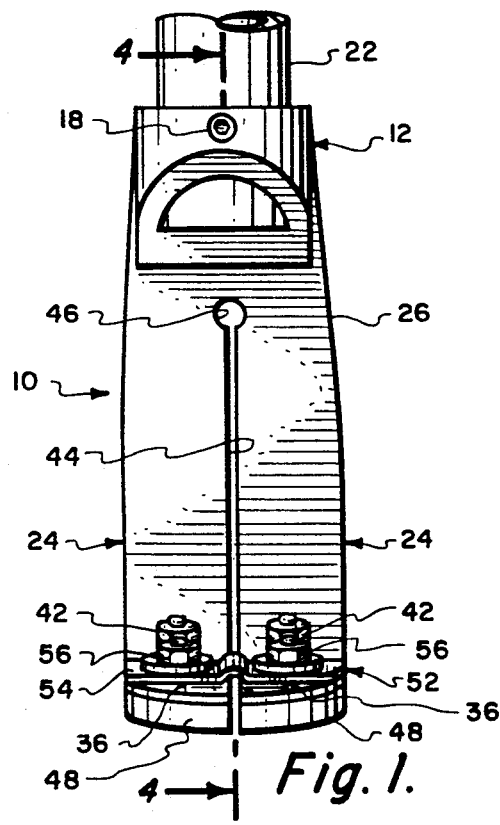
FIG. 1 is a front elevation view of a prosthesis constructed in accordance with the teachings of the invention.
Figure 2:
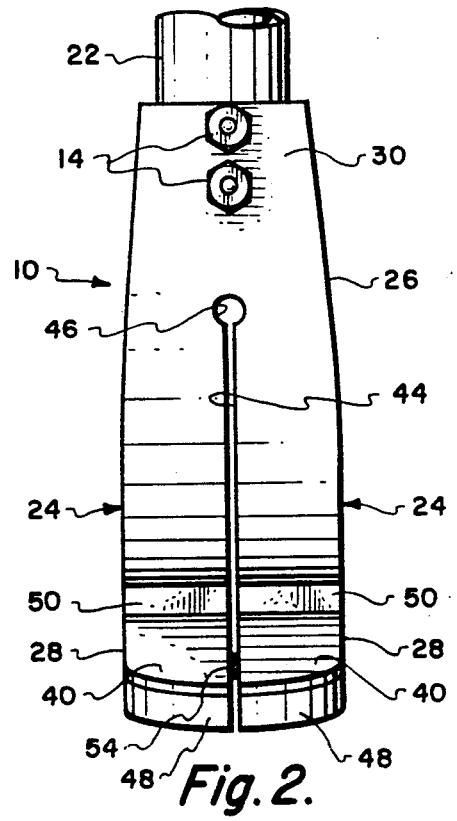
FIG. 2 is a rear elevation view of a prosthesis constructed in accordance with the teachings of the invention.
Figure 4:
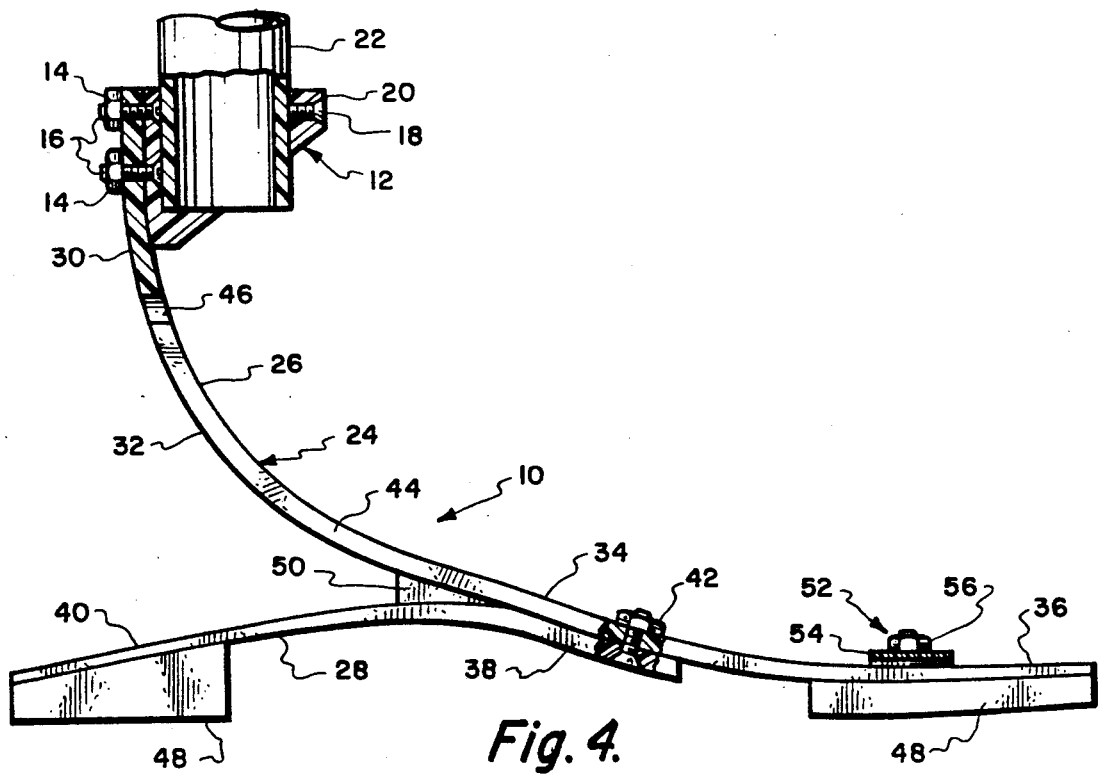
FIG. 4 is a partially cutaway side elevation sectional view, taken along line 4—4 of FIG. 1.

Referring to the drawings, and particularly to FIG. 4 thereof, I show a preferred embodiment of a foot prosthesis 10 constructed in accordance with the teachings of the invention and including attachment means 12 such as cooperating nuts 14, bolts 16, set screw 18, pylon 22 and coupling 20 for facilitating the operative engagement of the foot with a wearer's stump. Attached to the attachment means 12 and extending downwardly therefrom is a plurality of curvilinear foot portions 24, shown in the preferred embodiment as a bifurcated forefoot portion 26 and heel portions 28 secured thereto.

The foot portions 24 such as the preferred forefoot portion 26 further preferably include an attachment section 30, a curvilinear ankle section 32, FIG. 4, an arch section 34 and a toe section 36. The heel portions 28 preferably include an attachment section 38 and a heel section 40 projecting rearwardly therefrom. The various sections of the forefoot and heel portions, respectively, are preferably formed integrally with one another and simultaneously by the incorporation of a plurality of laminae embedded in a hardened, flexible polymer, similar to the fabrication methods taught in my above-noted patents.

The forefoot and heel portions of my invention, as well as the inventions of my above-noted patents, may also be manufactured by various other expedients, including injection molding and/or the use of thermoplastic materials and processes, or any of a range of combinations thereof.

Among other things, chopped fiber may be blended in a thermoplastic or thermoset resin and the resulting mixture injection molded into an appropriate configuration. Alternatively or additionally, thermoplastic laminae may be wound around an injection-molded core, or a thermoplastic resin may be injected between thermoplastic or thermoset laminae, whereby the laminates are bonded onto the injected material.

Figure 3:
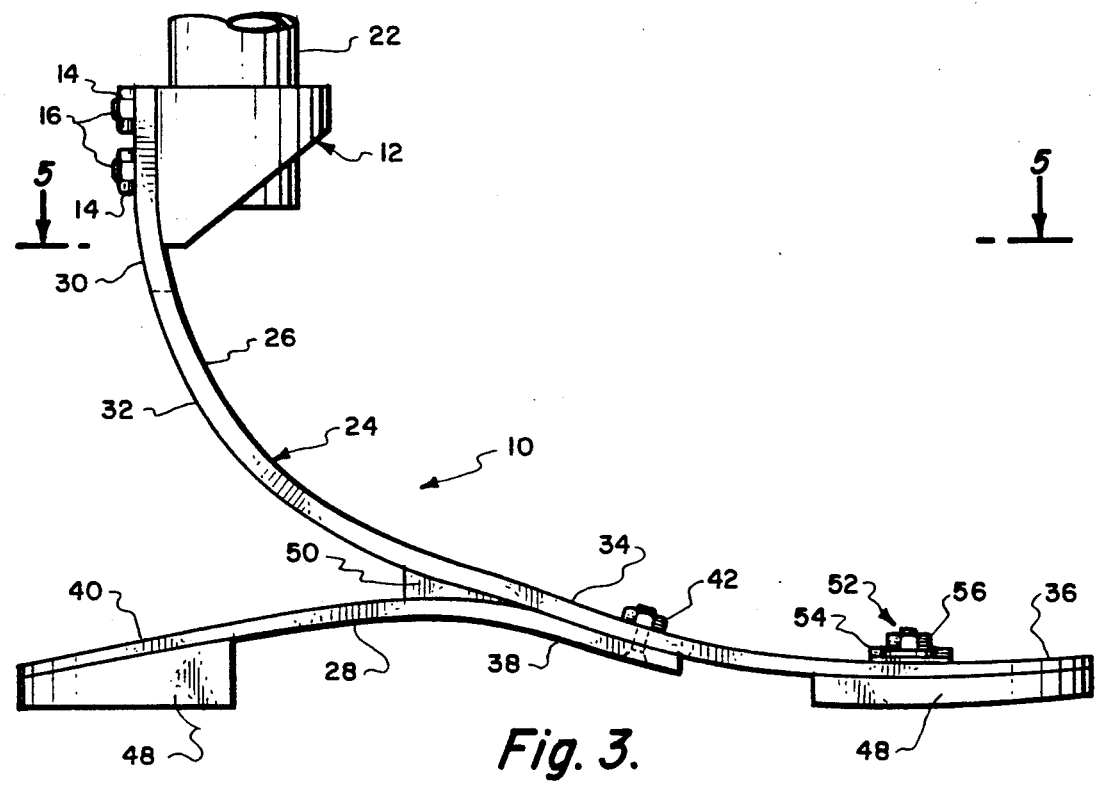
FIG. 3 is a side elevation view of a prosthesis constructed in accordance with the teachings of the invention.
Figure 5:
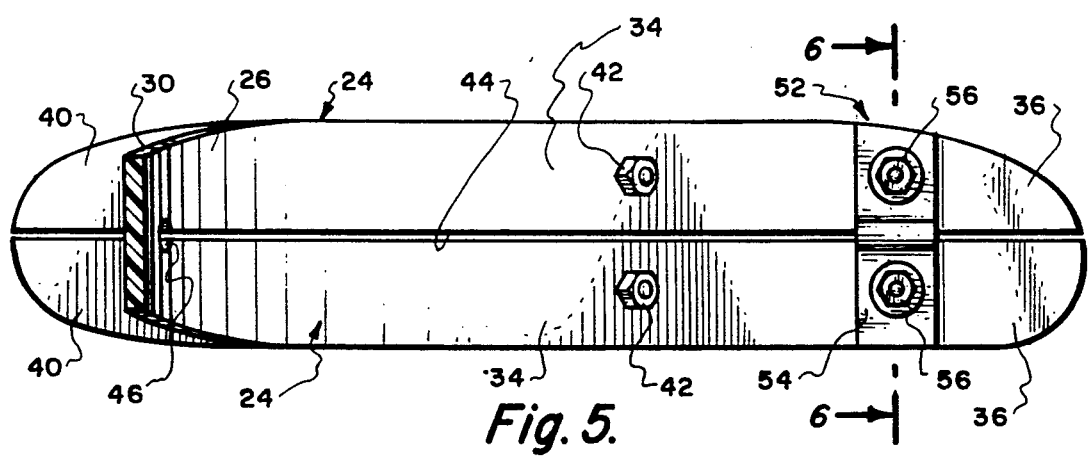
FIG. 5 is a partially sectional plan view taken along line 5—5 of FIG. 3 of a prosthesis constructed in accordance with the teachings of the invention.
Figure 6:
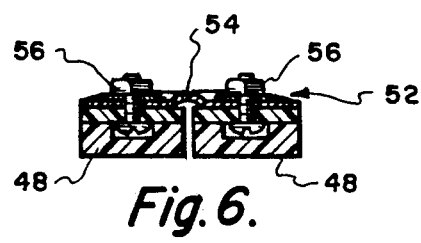
FIG. 6 is a sectional view, taken along line 6—6 of FIG. 5.

The attachment section 38 of the heel portions 28 are preferably secured to corresponding intersections of the curvilinear ankle sections 32 and the arch sections 34 of the curvilinear foot portions 24. Such securement may be permanent, through simultaneous and integral fabrication or through the use of epoxy, glue or the like, or may be demountable, FIGS. 3 and 4, through the utilization of bolt, nut and washer combinations 42 assembled through corresponding holes in the forefoot and heel portions 26 and 28. Demountable attachment is preferred, in that it permits forefoot portions to be selectably matched with any of various heel portions having different spring rates, as more fully discussed below.

As indicated above, the forefoot and heel portions 26 and 28 are preferably fabricated from superimposed laminates maintained in operative relationship by an encapsulating polymer and susceptible to bending stress determined by the thickness of the laminates. The preferred materials and fabrication process are more thoroughly described and explained in my above-mentioned U.S. Pat. Nos. 4,547,913 and 4,822,363, and include laminates such as carbon fibers and/or fiberglass or synthetic fibers such as Kevlar. Exemplary alternative methods and materials are described hereinabove.

As illustrated in the accompanying Figures, the forefoot portion 26 is preferably bifurcated into two foot portions 24, although additional multiple portions 24 (not shown) may be beneficially provided and utilized without departing from the scope of my invention.

Such bifurcation or further division may be accomplished through the incorporation of a slot 44 along the complete or substantially the complete length of the prosthesis 10. Such a slot 44 may be molded or subsequently cut into the prosthesis, or may be achieved by the juxtaposition of two or more completely separate foot portions 24 (not shown), each of which would be operatively attached to the attachment means 12. If the slot 44 is molded or cut into a single forefoot portion 26, stress relief means 46, such as a hole, is preferably provided at the upper end of the slot 44, to prevent undesired excessive loading and deterioration of the prosthesis at that location. Such a hole may be drilled or molded into the prosthesis 10.

The prosthesis of my invention is also preferably provided with underlying pads 48 and lever action blocks 50, as described in my aforementioned patents and pending applications. Such pad members may be affixed to the underside of the forefoot and heel portions, to create a profile for the bottom of the prosthesis 10 which corresponds to the interior of a shoe. Such a profile orients the foot 10, when the foot is in an unstressed state, at an appropriate angle for wearing shoes.

Additionally, the preferred embodiment of my invention includes retaining or connecting means 52 such as a strap 54 operatively attached to selected of the curvilinear foot portions 24 through the provision of nut, bolt and washer combinations 56 or the like. The strap 54 is preferably fabricated from impregnated canvas or other flexible, lightweight, tough material, and is located remote from the attachment section 30. By providing some play in the strap 54 rather than utilizing a taut strap, the selected foot portions 24 may flex independently of each other while exposed to lateral loading conditions, but will flex in a coordinated manner after sufficient movement has occurred to draw the strap taut. Thus, in extreme lateral loading conditions, more than one foot portion 24 will function to absorb and exert energy and prevent overload of a single foot portion 24.

It will be obvious to those skilled in the art that a virtually infinite variety of forefoot portions 26 and heel portions 28 may be fabricated, each having unique spring stress response characteristics determined by the configuration, composition and amount of the various component materials utilized therein. The aforementioned demountable connection of the heel portion to the forefoot portion therefore permits interchangeability of those portions to match the weight, stride and activity schedule of the wearer utilizing the prosthetic foot.

Those skilled in the art will understand that attachment means 12 have been described hereinabove merely by way of example, and that many alternative attachment means are available and may be utilized without departing from the scope of the invention.

The attachment section or sections 30, when assembled with the attachment means 12, are substantially rigid and capable of sustaining torsional, impact, and other loads impressed thereupon by the wearer during use of the foot 10. In addition, the inherent rigidity of the attachment section or sections prevents them from being distorted in any way and causes the effective transmission of the aforesaid loads imposed thereupon between the wearer and the prosthetic foot 10.

The forefoot and heel portions 26 and 28 can be provided with different numbers of laminates to make them more or less compliant to loads transmitted between the wearer and surface upon which the foot 10 is impacting. Consequently, when confronted with various anomalies in an amputee, such as an overweight condition or excess activity levels, the structure of the forefoot and heel portions can be materially modified to provide action which is precisely adjusted to the needs of the amputee. Moreover, a variety of forefoot and heel portions 26 and 28 can be made available to an amputee, allowing the flexibility of the prosthesis to be adjusted on the basis of the particular activity which the amputee is undertaking.

Those skilled in the art will understand that auxiliary flexure members (not shown) such as those described and shown in my co-pending applications Ser. Nos. 07/293,824 (see FIG. 7 therein) and 07/337,374 may be efficaciously utilized in connection with any embodiment of the abovedescribed invention, without departing from the scope of the teachings hereof.

In the preferred embodiment, the forefoot and heel portions 26 and 28 are constructed with some slight tapering of thickness along the length thereof, although those skilled in the art will understand that the invention is not limited to such tapering construction.

The materials from which the portions 26 and 28 are fabricated are preferably such as to provide an energy-storing, resilient, spring-like effect. This is because each engagement of the prosthetic foot 10 with an adjacent surface impresses compression, torsional, and other loads upon the prosthesis which must be stored within the prosthesis and then, dependent upon the stride of the wearer, be reimpressed upon said surface to achieve a natural stride conforming, ideally, in all respects to the stride of the unimpaired limb of the wearer of the prosthesis 10.

The multi-portioned prosthesis of my invention thus provides a compliance to lateral stresses and loading not previously achievable, and accomplishes this desirable result in a light-weight and responsive prosthesis. Moreover, the modularity of the invention permits the performance characteristics of the prosthesis to be fine-tuned and adjusted to the particular weight, size, and activity of the wearer.

As previously mentioned, the attachment section 30, the ankle section 32, the arch section 34, and the toe section 36 of the forefoot portion 26 are preferably formed integrally. Likewise, the attachment section 38 and the heel section 40 of the heel portion 28 are preferably formed integrally. The configuration of these sections is the means whereby bending and compressive loads imposed during impingement of the prosthetic foot 10 upon an adjacent surface are absorbed and subsequently reimposed upon said surface. These various sections are so designed that they function, substantially, to permit some flexure of the portions 26 and 28. In combination with the multiple foot portions 24, the prosthesis 10 functions in a manner analogous to a normal foot and normal ankle joint, permitting the wearer to experience a more natural gait and feel with the prosthesis than was possible with prior art prostheses.

The prosthetic foot of my invention can thus be provided in different sizes to correspond to the size of the natural foot of the wearer of the prosthesis 10. When such different sizes are provided, corresponding reduction or increase in the number of laminae and thickness of taper, if any, of the respective sections of the forefoot and heel portions 26 and 28 can be made to provide for the proper flexure of said sections.

Moreover, the flexibility of the prosthetic foot of my invention may be further increased, while still maintaining acceptable strength characteristics, by providing an auxiliary ankle member o an auxiliary forefoot portion (not shown, but similar to that illustrated in my co-pending application Ser. No. 07/337,374). Such an auxiliary member or portion would be operatively affixed to the forefoot portions 26 to provide some relative movement therebetween.

The aforementioned flexure of the various foot portions 24 provides the capacity for increased surface area contact between the bottom of the prosthesis 10 and a confronting supporting surface during both the impact and delivery phases of lateral loading of the prosthesis 10. Instead of a single edge of the prosthesis effectively contacting the supporting surface, the above-described independent flexure of the portions 24 permits corresponding edges of each such portion 24 to contact the supporting surface, thereby improving the traction or frictional contact between the bottom of the prosthesis and the confronting surface.

The prosthesis of my invention has been described with some particularity but the specific designs and constructions disclosed are not to be taken as delimiting of the invention in that various modifications will at once make themselves apparent to those of ordinary skill in the art, all of which will not depart from the essence of the invention and all such changes and modifications are intended to be encompassed within the appended claims.

I claim:

1. In a prosthetic foot, the combination of: attachment means for facilitating the operative engagement of the foot with a wearer's stump; and a plurality of curvilinear, energy-storing foot portions operatively attached to said attachment means and extending downwardly therefrom to contact a supporting surface, each of said foot portions including an ankle section, whereby said foot portions may interact with the supporting surface independently from one another, in which said plurality of curvilinear portions are of similar shape.

2. The prosthetic foot of claim 1 in which one or more of said plurality of curvilinear portions include forwardly extending forefoot sections having rearwardly extending heel sections operatively connected thereto.

3. The prosthetic foot of claim 2 in which said heel sections are detachably connected to said forefoot sections.

4. The prosthetic foot of claim 1 or claim 2 or claim 3, further including connecting means for operatively connecting two or more of said plurality of curvilinear portions to each other at a location remote from said attachment means, whereby the movement of said connected curvilinear portions relative to each other is limited.

5. The prosthetic foot of claim 1 or claim 2 or claim 3 in which said plurality of curvilinear portions is fabricated from superimposed laminates maintained in operative relationship by an encapsulating polymer and susceptible to bending stress determined by the thickness of the laminates.

6. The prosthetic foot of claim 1 or claim 2 or claim 3 in which said plurality of curvilinear portions include continuous, integrally and simultaneously formed attachment, ankle, arch and toe sections, said sections being fabricated as unitary structures by polymer impregnation of superimposed reinforcing laminae; said attachment, ankle, arch and toe sections being capable of spring stress generated energy storage whereby the subjection of said foot to bending moments will cause transmission of spring stress through said attachment, ankle, arch and toe sections.

7. The prosthetic foot of claim 6, further including a corresponding plurality of heel members having a attachment section secured to the intersection of said arch and toe sections and a heel section extending rearwardly therefrom, said heel members being fabricated as unitary structures by polymer impregnation of superimposed reinforcing laminae and being capable of spring stress generated energy storage.

8. A prosthetic foot including: a forefoot portion incorporating an upper attachment section for facilitating operative connection to a wearer's stump, a curvilinear ankle section, an arch section and a toe section; and a heel portion having an attachment section secured to said forefoot portion and a heel section extending therefrom, in which said forefoot and heel portions are completely or partially divided into similarly-shaped segments capable of movement relative to one another.

9. The prosthetic foot of claim 8 in which said division into segments constitutes a bifurcation of said forefoot and heel portions.

10. The prosthetic foot of claim 9 in which said bifurcation is defined by a slot in said forefoot and heel portions.

11. The prosthetic foot of claim 8 in which said securement of said heel portion to said forefoot portion occurs at the intersection of said arch and toe sections.

12. The prosthetic foot of claim 8, further including connecting means for operatively connecting two or more of said segments to each other at a location remote from said attachment section, whereby the movement of said connected segments relative to each other is limited.

13. The prosthetic foot of claim 8 or claim 9 or claim 10 or claim 11 or claim 12 in which said securement of said heel portion to said forefoot portion is detachable.

14. The prosthetic foot of claim 8 or claim 9 or claim 10 or claim 11 or claim 12 in which said heel portion is fabricated from superimposed laminates maintained in operative relationship by an encapsulating polymer and susceptible to bending stress determined by the thickness of the laminates.

15. The prosthetic foot of claim 8 or claim 9 or claim 10 or claim 11 or claim 12 in which said forefoot portion is fabricated from superimposed laminates maintained in operative relationship by an encapsulating polymer and susceptible to bending stress determined by the thickness of the laminates.

16. The prosthetic foot of claim 8 or claim 9 or claim 10 or claim 11 or claim 12 in which said forefoot portion consists of continuous, integrally and simultaneously formed attachment, ankle, arch and toe sections, said sections being fabricated as unitary structures by polymer impregnation of superimposed reinforcing laminae; said attachment, ankle, arch and toe sections being capable of spring stress generated energy storage whereby the subjection of said foot to bending moments will cause transmission of spring stress through said attachment, ankle, arch and toe sections.

17. The prosthetic foot of claim 16 in which said heel portions are demountably attached to corresponding of said forefoot portions to permit heel portions having different spring rates to be secured to said forefoot portions of said foot.

18. The prosthetic foot of claim 8 or claim 9 or claim 10 or claim 11 or claim 12 in which said heel portions consist of continuous, integrally and simultaneously formed attachment and heel sections, said sections being fabricated as unitary structures by polymer impregnation of superimposed reinforcing laminae; said attachment and heel sections being capable of spring stress generated energy storage whereby the subjection of said foot to bending moments will cause transmission of spring stress through said attachment and heel sections.

19. In a prosthetic foot, the combination of, attachment means for facilitating the operative engagement of the foot with a wearer's stump; and a bifurcated, curvilinear, energy-storing foot portion operatively attached to said attachment means and extending downwardly therefrom to contact a supporting surface, said bifurcation of said foot portion extending in an anterior/posterior direction with respect to the wearer and including substantially all of said foot portion, whereby the resulting bifurcated sections of said foot portion may interact with the supporting surface independently from one another.

20. The prosthetic foot of claim 19, in which said bifurcated curvilinear foot portion includes a forefoot portion and a bifurcated heel portion detachably mounted thereto.

* * * * *